United States Patent
Koogle, Jr. et al.

(10) Patent No.: US 10,363,024 B2
(45) Date of Patent: Jul. 30, 2019

(54) SYSTEM FOR MENISCAL REPAIR USING SUTURE IMPLANT CINCH CONSTRUCT

(71) Applicant: Arthrex, Inc., Naples, FL (US)

(72) Inventors: David C. Koogle, Jr., Bonita Springs, FL (US); Ricardo Albertorio, Naples, FL (US); Jacob A. Jolly, Naples, FL (US); Vipool K. Goradia, Midlothian, VA (US)

(73) Assignee: Arthrex, Inc., Naples, FL (US)

(*) Notice: Subject to any disclaimer, the term of this patent is extended or adjusted under 35 U.S.C. 154(b) by 532 days.

(21) Appl. No.: 14/608,623

(22) Filed: Jan. 29, 2015

(65) Prior Publication Data

US 2015/0142052 A1    May 21, 2015

Related U.S. Application Data (63) Continuation of application No. 12/397,272, filed on Mar. 3, 2009, now Pat. No. 8,961,538.

(60) Provisional application No. 61/033,644, filed on Mar. 4, 2008.

(51) Int. Cl.
*A61B 17/04* (2006.01)

(52) U.S. Cl.
CPC ...... *A61B 17/0401* (2013.01); *A61B 17/0467* (2013.01); *A61B 17/0469* (2013.01); *A61B 17/0482* (2013.01); *A61B 2017/0409* (2013.01); *A61B 2017/0417* (2013.01); *A61B 2017/0464* (2013.01); *A61B 2017/0474* (2013.01); *A61B 2017/0496* (2013.01)

(58) Field of Classification Search
CPC ........... A61B 17/04; A61B 17/0401; A61B 2017/0409; A61B 2017/0411
See application file for complete search history.

(56) References Cited

U.S. PATENT DOCUMENTS

| | | | |
|---|---|---|---|
| 3,845,772 A | 11/1974 | Smith | |
| 4,235,238 A | 11/1980 | Ogiu et al. | |
| 5,224,946 A * | 7/1993 | Hayhurst | A61B 17/0401 606/139 |
| 5,258,016 A * | 11/1993 | DiPoto | A61B 17/0401 606/104 |
| 5,417,691 A | 5/1995 | Hayhurst | |
| 5,683,401 A * | 11/1997 | Schmieding | A61B 17/0485 606/104 |
| 5,697,931 A * | 12/1997 | Thompson | A61B 17/0401 128/898 |
| 5,782,862 A * | 7/1998 | Bonutti | A61B 17/0401 606/104 |
| 6,500,184 B1 * | 12/2002 | Chan | A61B 17/0482 606/144 |
| 6,554,852 B1 * | 4/2003 | Oberlander | A61B 17/0401 606/104 |
| 6,626,930 B1 * | 9/2003 | Allen | A61B 17/0401 606/213 |

(Continued)

*Primary Examiner* — Dianne Dornbusch
(74) *Attorney, Agent, or Firm* — Carlson, Gaskey & Olds (57) ABSTRACT

A system for repairing tears in soft tissue, e.g., meniscal tissue, by employing cinch stitching. More specifically, the present invention provides an apparatus for meniscal repair using a suture implant construct. The suture implant construct includes a first and second implant which are connected to each other via a length of suture. The implants are designed to be loaded on external surfaces of the first and second trocars.

18 Claims, 11 Drawing Sheets

(56) References Cited

U.S. PATENT DOCUMENTS

| | | | |
|---|---|---|---|
| 6,635,073 B2 * | 10/2003 | Bonutti | A61B 17/0401 606/216 |
| 6,656,182 B1 | 12/2003 | Hayhurst | |
| 6,716,234 B2 | 4/2004 | Grafton et al. | |
| 7,909,836 B2 * | 3/2011 | McLean | A61B 17/0401 606/139 |
| 8,512,375 B2 * | 8/2013 | Torrie | A61B 17/0401 606/232 |
| 8,702,718 B2 * | 4/2014 | Bhatnagar | A61B 17/064 606/99 |
| 8,708,885 B2 * | 4/2014 | Khamis | A61B 17/00234 600/37 |
| 9,314,235 B2 * | 4/2016 | Bojarski | A61B 17/0401 |
| 2003/0236535 A1 * | 12/2003 | Onuki | A61B 17/0482 606/144 |
| 2005/0033363 A1 * | 2/2005 | Bojarski | A61B 17/0401 606/228 |
| 2006/0030885 A1 | 2/2006 | Hyde | |
| 2006/0142799 A1 * | 6/2006 | Bonutti | A61B 17/0401 606/232 |
| 2006/0178680 A1 * | 8/2006 | Nelson | A61B 17/0401 606/139 |
| 2007/0027476 A1 * | 2/2007 | Harris | A61B 17/0401 606/232 |
| 2007/0073319 A1 * | 3/2007 | Mikkaichi | A61B 5/117 606/153 |
| 2007/0073322 A1 * | 3/2007 | Mikkaichi | A61B 17/0057 606/153 |
| 2007/0100350 A1 * | 5/2007 | Deffenbaugh | A61B 17/0401 606/104 |
| 2007/0142838 A1 * | 6/2007 | Jordan | A61B 17/0401 606/75 |
| 2008/0065120 A1 * | 3/2008 | Zannis | A61B 17/0401 606/144 |
| 2008/0140092 A1 * | 6/2008 | Stone | A61B 17/0401 606/144 |
| 2008/0140093 A1 * | 6/2008 | Stone | A61B 17/0401 606/144 |

* cited by examiner

FIG. 6

FIG. 7
DETAIL B

FIG. 8
DETAIL C

SYSTEM FOR MENISCAL REPAIR USING SUTURE IMPLANT CINCH CONSTRUCT

CROSS-REFERENCE TO RELATED APPLICATIONS

This is a divisional of application Ser. No. 12/397,272, filed Mar. 3, 2009, now U.S. Pat. No. 8,961,538, which claims the benefit of U.S. Provisional Application No. 61/033,644, filed Mar. 4, 2008, the entire disclosure of which is incorporated by reference herein.

FIELD OF THE INVENTION

The present invention relates to methods of arthroscopic surgery and, more specifically, to an improved method of repairing tears in tissue, such as meniscal tissue.

BACKGROUND OF THE INVENTION

Tissue repair requires the surgeon to pass suture material through selected tissue, form a plurality of surgical knots extracorporeally and then move the knots into position adjacent the desired tissue to be sutured. In such procedures, the surgeon must manually tie the knots on the suture strands after the suture is threaded through the selected tissues to be sutured. Knot tying during surgery, particularly arthroscopic surgery, is tedious and time-consuming. There is also a tendency for the knots to deform or collapse as the surgeon manually forces the knots down into the proper position.

Accordingly, a need exists for an improved method of repairing tears in soft tissue (such as the meniscus) which does not require multiple suture knots.

SUMMARY OF THE INVENTION

The present invention provides a system and method for repairing tears in soft tissue, e.g., meniscal tissue, by employing cinch stitching. More specifically, the present invention provides apparatus and methods for meniscal repair using a suture implant construct. The suture implant construct comprises a first and second implant which are connected to each other via a length of suture. The implants are designed to be loaded on external surfaces of the first and second trocars.

Other features and advantages of the present invention will become apparent from the following description of the invention, which refers to the accompanying drawings.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The present invention provides methods and systems for repairing tears in soft tissue (such as the meniscus) employing cinch stitching. In particular embodiments, the present invention provides a meniscal cinch assembly comprising first and second trocars, a depth stop adapted to securely engage one of the trocars, and a suture implant construct configured to be loaded onto external surfaces of the first and second trocars of the meniscal cinch assembly.

The suture implant construct of the present invention comprises a first and second implant which are connected to each other via a length of suture. The implants are designed to be loaded on external surfaces of the first and second trocars. Each implant has a through-hole running in a direction parallel to the longitudinal axis of the implant and through which suture is inserted. As detailed below, the implants are configured with opposing planar end faces that are perpendicular to the longitudinal axis of the implant.

The present invention also provides methods for soft tissue fixation (such as meniscal repair, for example) by cinch stitching. According to an exemplary embodiment, the method comprises the steps of: (i) providing a meniscal cinch assembly comprising first and second trocars, a depth stop adapted to securely engage one of the trocars, and a suture implant construct having first and second implants loaded on the external surface of the first and second trocars; and (ii) passing at least one of the first and second implants through tissue to be repaired (for example, labral tissue of the glenoid or meniscal knee tissue).

Figure 22:
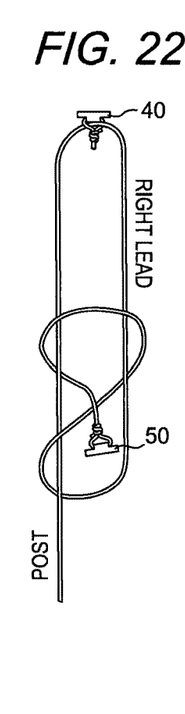
Figure 23:
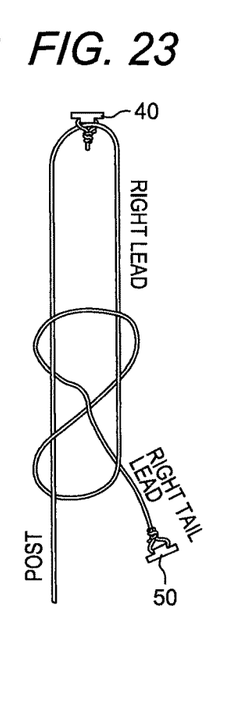
Figure 24:
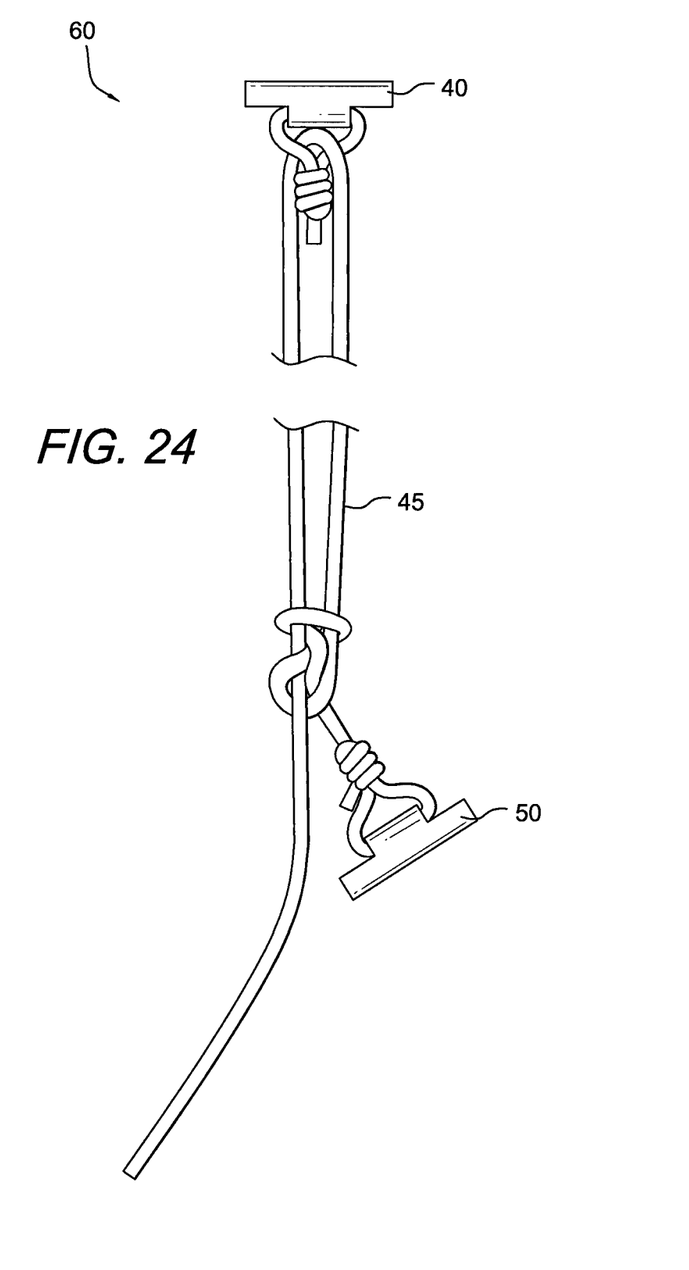

Referring now to the drawings, where like elements are designated by like reference numerals, FIGS. 1-13 illustrate a meniscal cinch assembly 100 of the present invention (comprising first and second trocars 10, 20; depth stop 30; and first and second implants 40, 50). FIGS. 14-17 illustrate implant 40 used with the meniscal cinch assembly 100 of the present invention. FIGS. 18-23 illustrate various steps in the formation of a knot assembly suture construct 60 (comprising first and second implants 40, 50 attached by a flexible strand 45) used with the meniscal cinch assembly 100 of the present invention. FIG. 24 illustrates the final knot assembly suture construct 60 of FIG. 23. FIGS. 25-35 illustrate various steps of a method of arthroscopic repair using the meniscal cinch assembly 100 of the present invention.

Reference is now made to FIGS. 1-13 which illustrate meniscal cinch assembly 100 of the present invention including an actuating mechanism configured to operate a suture implant construct. As shown in the drawings, meniscal cinch assembly 100 (FIGS. 5, 12 and 13) comprises a push rod assembly 110 (a trocar assembly 110) (FIGS. 1-4), a suture implant construct 60 (FIG. 9) fully seated onto the trocar assembly 110, and a delivery system 120 (FIG. 11) for releasing and advancing implants of the suture implant construct 60 onto the exterior surface of a meniscus.

As shown in FIGS. 1-4, trocar assembly 110 of the meniscal cinch assembly 100 comprises a first trocar 10 in communication with a second trocar 20, the first and second trocars being designed to carry onto their external surfaces a first implant 40 (on the first trocar 10) and a second implant 50 (on the second trocar 20).

Figure 1:
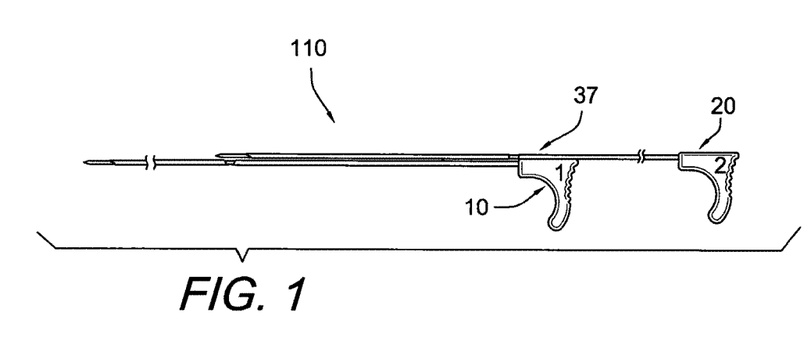
FIG. 1 illustrates a side view of a first and second trocars of a meniscal cinch assembly according to an embodiment of the present invention.
Figures 2, 3:
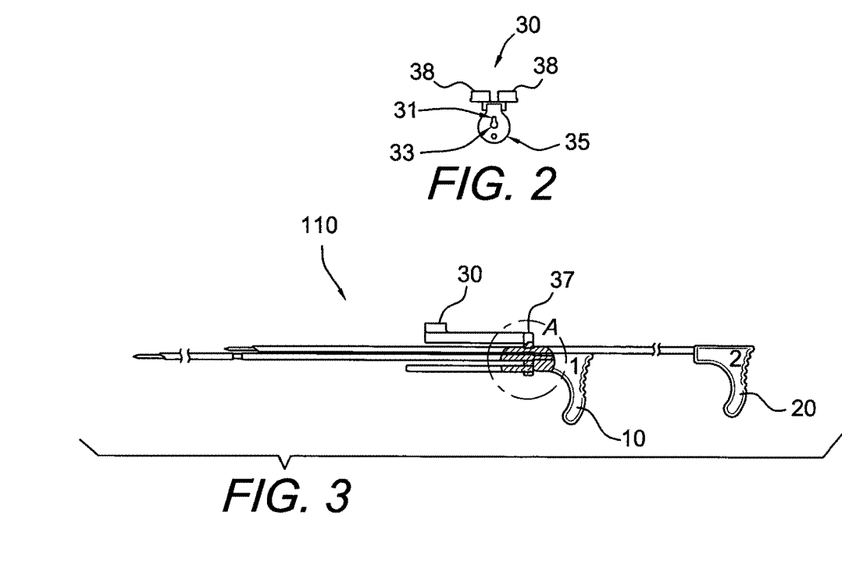
FIG. 2 is a side view of the depth stop to be assembled to the first and second trocars of FIG. 1.
FIG. 3 illustrates a side view of first and second trocars of FIG. 1 (with a depth stop attached)

FIG. 2 illustrates depth stop 30 of the meniscal cinch assembly 100 comprising an upper slot 31, a lower slot 33, and a depth slot 35. Depth stop 30 is designed to ensure appropriate release of the first and second implants 40, 50 into the meniscal tissue to be repaired (i.e., it limits the protrusion distance of the implant loaded trocar beyond the tip of the meniscal cinch cannula 100). Uncontrolled advancement of the implants into the damaged meniscal tissue may have unwanted consequences and may require additional repair steps.

Figure 4:
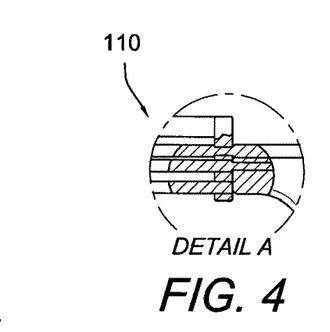
FIG. 4 illustrates an enlarged view of the detail A of FIG. 3.
Figure 5:
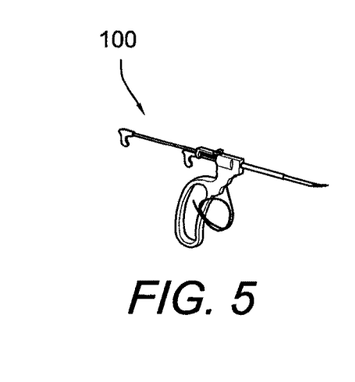
FIG. 5 illustrates a perspective view of the meniscal cinch assembly of the present invention.
Figure 6:
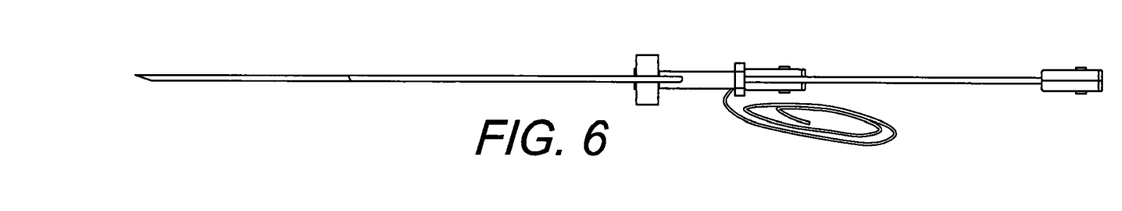
FIG. 6 illustrates a top view of the meniscal cinch assembly of the present invention with a first and second implant seated.

In use, the second trocar 20 is slid into the bottom hole of the depth stop 30 to machined groove 37 (FIGS. 1 and 3) and snapped upward into the upper slot 31 of depth stop 30 to secure (see detail A of FIG. 4). The first trocar 10 is slid into the bottom hole of the depth stop 30 until the handle mates with depth stop 30, as shown in FIG. 3.

Figure 7:
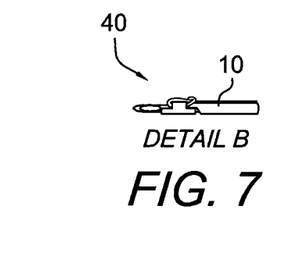
FIG. 7 illustrates a side view of the first implant of the meniscal cinch assembly of FIG. 6.
Figure 8:
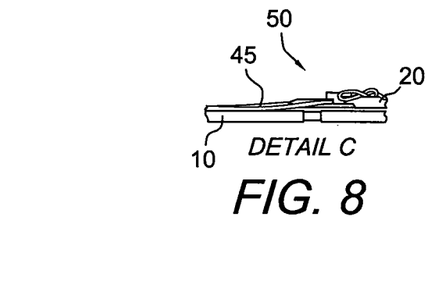
FIG. 8 illustrates a side view of the second implant of the meniscal cinch assembly of FIG. 6.
Figure 9:
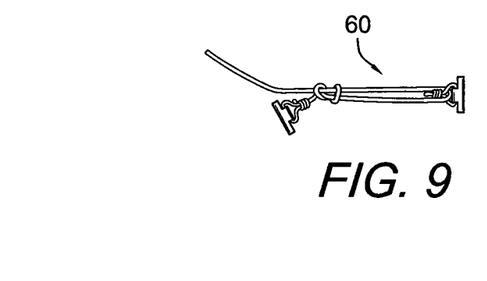
FIG. 9 illustrates a side view of the first and second implants of the meniscal cinch assembly of FIG. 6, connected by a flexible strand.

FIGS. 6-10 illustrate the suture construct 60 with connected first and second implants 40, 50 mounted on the first and second trocars 10, 20. The suture construct is assembled to the first and second trocars 10, 20 by sliding the long lead first implant 40 onto the first trocar 10, oriented and fully seated as shown in FIG. 7 (detail B). Without twisting the suture leads, short lead second implant 50 is slid onto the second trocar 20, oriented and fully seated as shown in FIG. 8 (detail C). With implants 40, 50 fully seated, ensure that slight suture slack between implants is acceptable, and also that the suture is laying against the trocars 10, 20 and the free end is not twisted around the suture construct, trocars or depth stop. The sliding knot must not be tensioned tight and located beyond the second implant. Preferably, the construct 60 is loose and tangle free before insertion.

The implants 40, 50 may be formed of PEEK or similar material and flexible strand 45 may be a suture and/or may comprise a bioabsorbable material, such as PLLA or one of the other polylactides, for example, and/or may be formed of twisted fibers having strands of a contrasting color added to the braided threads, to make the suture more visible during surgical procedures. In exemplary embodiments, strand 45 may contain strands of a high strength suture material, such as Arthrex FiberWire® suture disclosed in U.S. Pat. No. 6,716,234, incorporated herein by reference.

Figure 10:
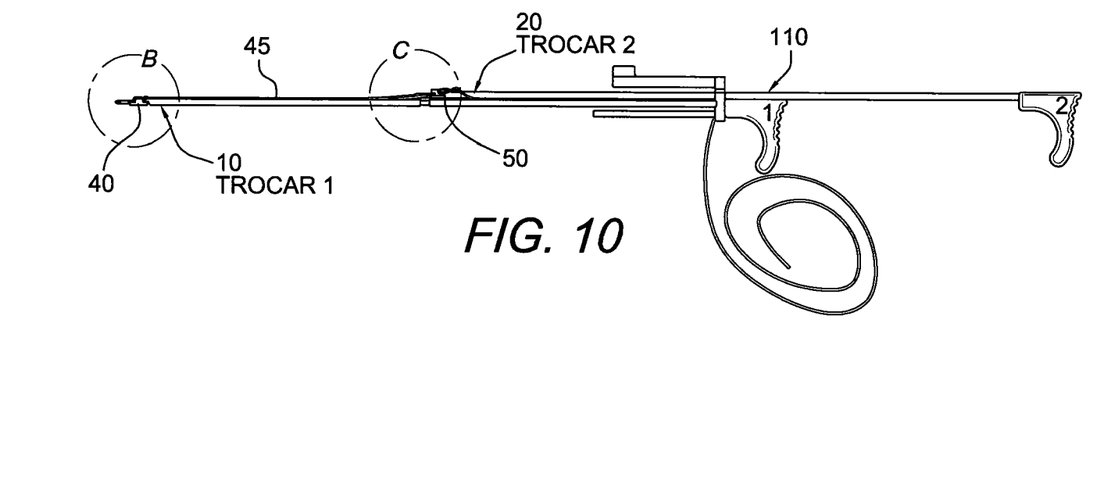
FIG. 10 illustrates a side view of the meniscal cinch assembly of the present invention with a first and second implant seated.
Figures 11, 12, 13:
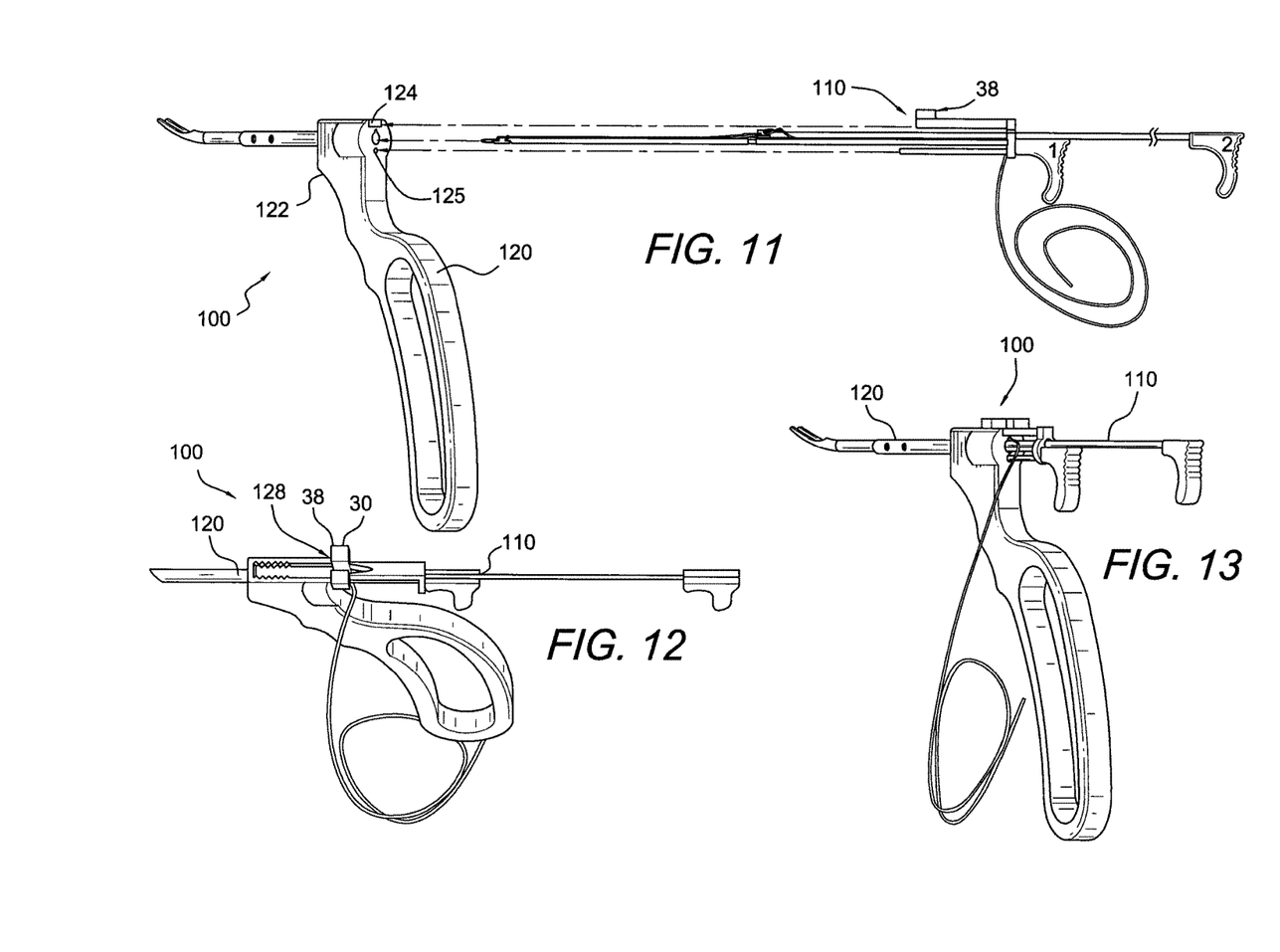
FIG. 11 illustrates a perspective view of the first and second trocars of the meniscal cinch assembly of the present invention, prior to sliding the trocar/suture assembly within the delivery hand piece.
FIG. 12 illustrates another perspective view of the meniscal cinch assembly of the present invention.
FIG. 13 illustrates another perspective view of the meniscal cinch assembly of the present invention.

Reference is made to FIGS. 11-13. The subassembly 110 of FIG. 10 is slid into appropriate holes 122 and ratchet grooves 124 of delivery device 120 (FIG. 11) to obtain the meniscal cinch assembly 100 shown in FIGS. 12 and 13. The subassembly 110 is slid in until reaching depth stop 30. The tabs 38 of depth stop 30 are squeezed together to advance the subassembly 110 to first ratchet tooth 128 (FIG. 12). The tabs 38 of the stop depth 20 are then released to secure the subassembly in the docked position.

As detailed below, when the first trocar is pulled from the meniscus, the first implant 40 makes contact with the meniscal tissue and, as a result, is released from the exterior surface of the first trocar 10. As the first implant 40 is released from the exterior surface of the first trocar 10, it flips about 90-degrees and becomes secured on the exterior surface of the meniscus. The first trocar 10 is then fully removed from the cannula. The operation is repeated with the second trocar 20 loaded with the second implant 50. Once the second implant 50 is released, the implant flips about 90-degrees and becomes secured on the exterior surface of the meniscus adjacent to the first implant 40. The meniscal cinch assembly is then removed from the knee.

Figure 14:
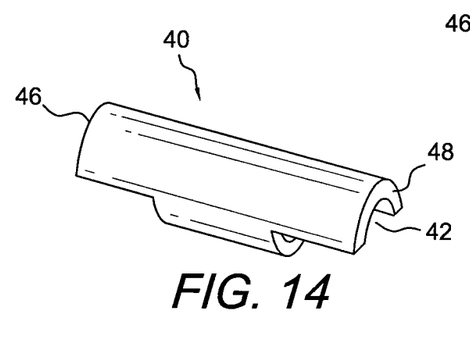
FIG. 14 illustrates a perspective view of an implant used with the meniscal cinch assembly of the present invention.
Figure 15:
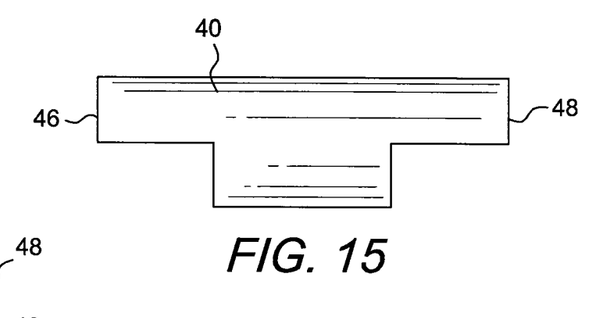
FIG. 15 illustrates a side view of the implant of FIG. 14.
Figure 16:
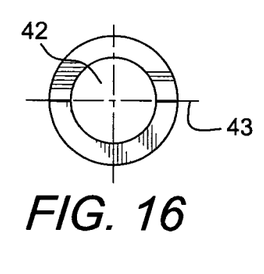
FIG. 16 illustrates a lateral view of the implant of FIG. 14.
Figure 17:
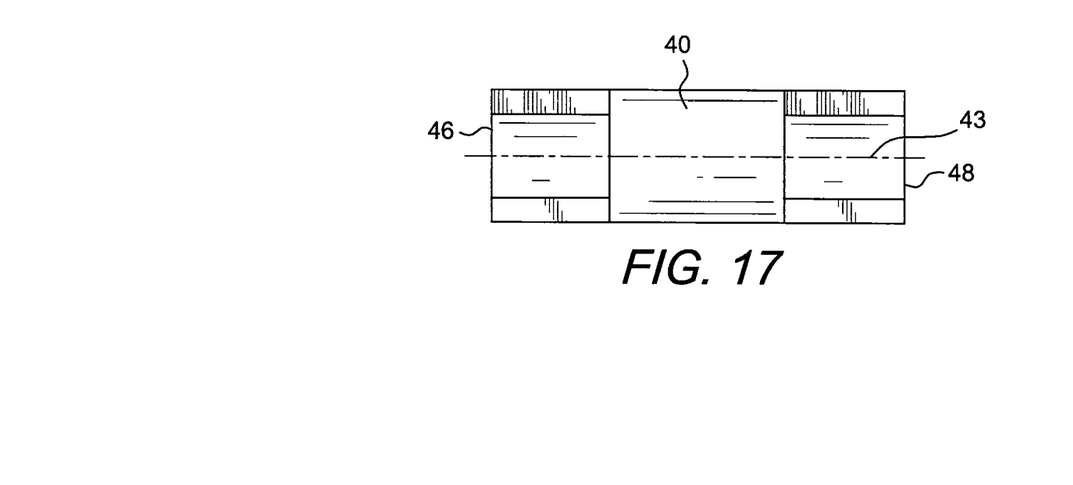
FIG. 17 illustrates a bottom view of the implant of FIG. 14.

FIGS. 14-17 illustrates various views of implant 40 used with the meniscal cinch assembly 100 of the present invention. As shown in FIG. 14, for example, the implant has a cannulation 42 in a direction about parallel to the longitudinal axis 43 of the implant and through which suture is inserted. The implant also has opposing end faces 46, 48 (FIG. 14) that are about perpendicular to the longitudinal axis of the implant.

FIGS. 18-24 illustrate various steps in the formation of a knot assembly suture construct 60 (comprising first and second implants 40, 50 attached by a strand 45) used with the meniscal cinch assembly 100 of the present invention. FIG. 24 illustrates the final knot assembly suture construct 60 of FIG. 23. Knot assembly suture construct 60 withstands about 45N tensile pull test.

Figures 18, 19:
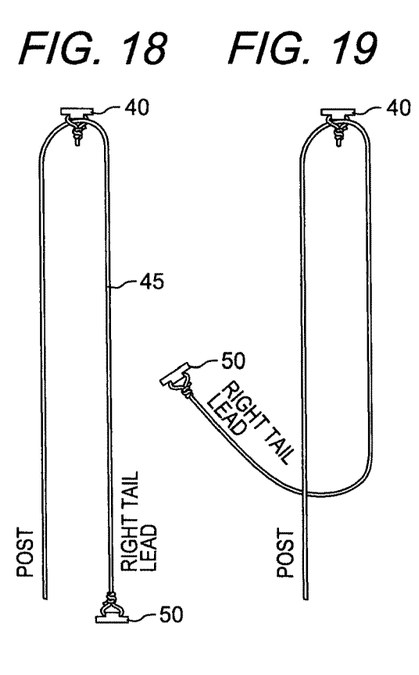
FIGS. 18-24 illustrates various steps in the formation of a knot assembly suture construct used with the meniscal cinch assembly of the present invention.
Figures 20, 21:
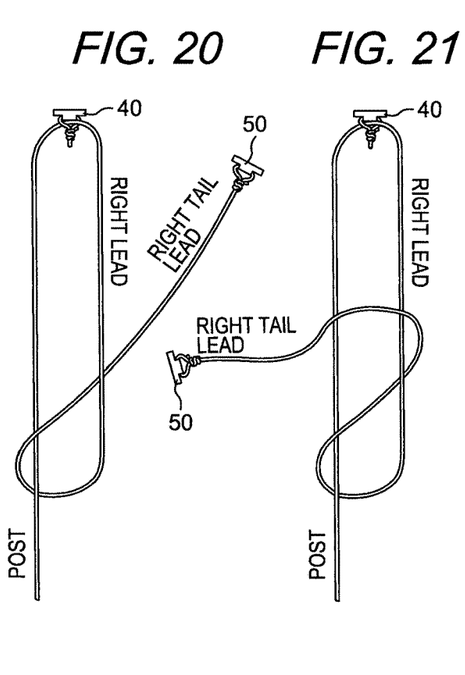

In use, a single braided implant construct is threaded onto prebraided long suture 45 (for example, an 18 inch suture) oriented as shown in FIG. 18. The right tail lead is wrapped under the post, as shown in FIG. 19. The tail lead is wrapped over the post and passed through opening exiting out under the right lead, as shown in FIG. 20. The tail is wrapped around the right lead and post, as shown in FIG. 21. The tail is wrapped around the post back toward opening and over cross lead, as illustrated in FIG. 22. The tail is tucked in the second opening, exiting out under the right lead (FIG. 23). The sliding knot is tensioned down to the desired dimension (FIG. 24) to obtain the final construct 60.

Reference is now made to FIGS. 25-35 which illustrate various steps of a method of arthroscopic repair using the meniscal cinch assembly 100 of the present invention. The methods of the present invention distribute suture pressure to tissue, reduce tissue cut, and allow for accelerated tissue healing that is achieved with minimal knot tying.

For exemplary purposes only, the invention will be described below with reference to an arthroscopic meniscal knee joint repair. However, the invention is not limited to this exemplary embodiment and has applicability to any reattachment of tissue to tissue (for example, reattachment of labral tissue (cartilage) to the glenoid).

FIGS. 25-35

Figure 25:
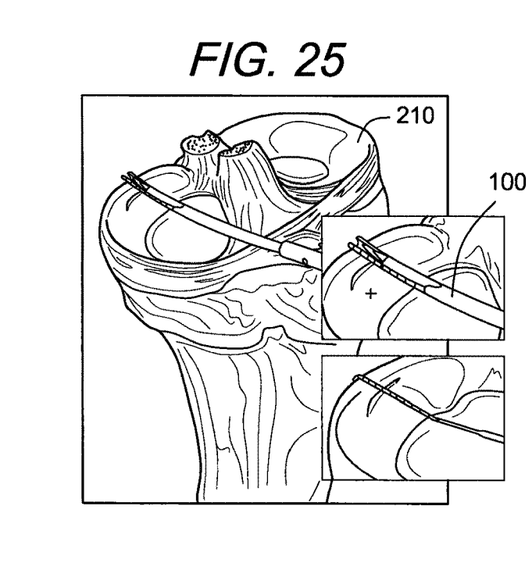
FIGS. 25-35 illustrate various steps of a method of arthroscopic repair using the meniscal cinch assembly of the present invention.

The repair 200 (FIG. 35) according to an exemplary cinch stitching technique of the present invention includes the following steps:

FIG. 25: The meniscal cinch is designed to be used through a low arthroscopic portal, near the surface of the tibia 210. A measurement is taken to approximate the distance between the entry point of the implant 40, 50 to the knee capsule. The measurement can be taken with either a measurement probe or the graduated tip of the meniscal cinch cannula (where each line represents about 2 mm).

Figure 26:
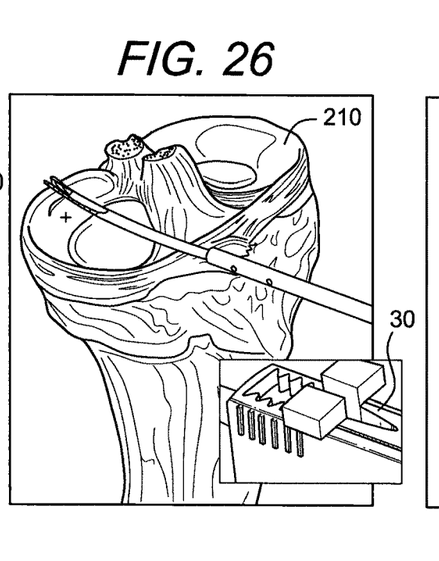

FIG. 26: The depth stop 30 on the meniscal cinch handle is set to the distance measured above, by squeezing the tips together and sliding the depth stop 30 forward. The depth stop 30 is set to a distance about equal to the measurement in the step of FIG. 25. Each line on the handle represents about 2 mm.

Figure 27:
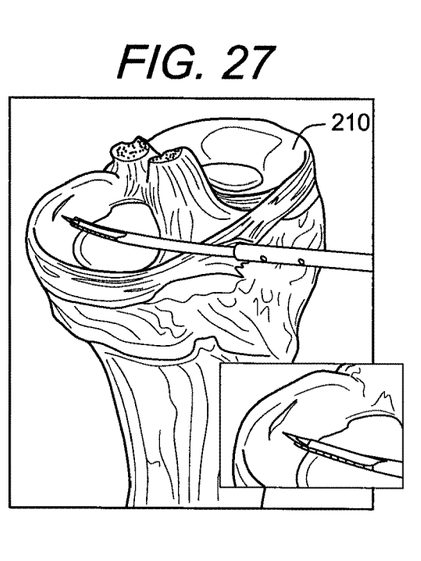

FIG. 27: A cannula (for example, a shoehorn cannula) may be placed into the working portal before inserting the meniscal cinch device 100. Place the tip of the meniscal cinch cannula near the tear. The tip of the cannula may be used to reduce the tear prior to deployment of the first trocar 10. Alternatively, the tip of the first trocar may be advanced past the tip of the cannula to be used to reduce the tear. The trocar should not be pulled back into the cannula after it has been advanced as it could prematurely deploy the implant.

Figure 28:
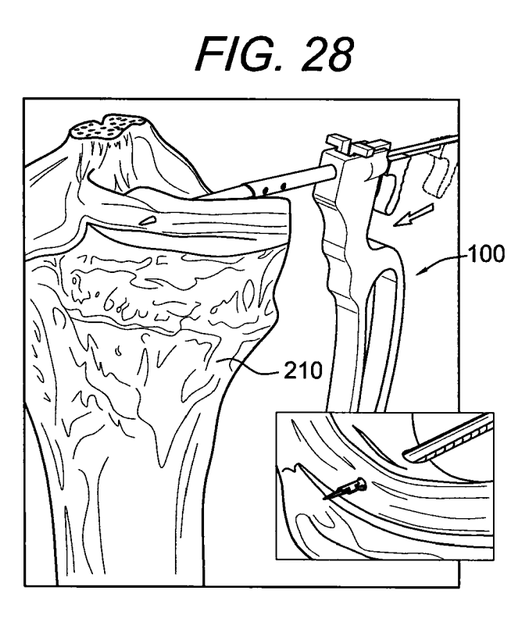

FIG. 28: The tip of the meniscal cinch cannula is placed in contact with, but does not pierce, the meniscus near the meniscal tear. The first implant 40 is advanced through the meniscus by pushing the first trocar 10 forward until the trocar handle makes contact with the depth stop 30 and the cannula rests on the surface of the meniscus. As the first trocar 10 is pulled from the meniscus, the first implant 40 makes contact with the meniscal tissue and as a result is released from the exterior surface of the first trocar 10. As the first implant 40 is released from the exterior surface of the first trocar 10, it flips about 90-degrees and becomes secured on the exterior surface of the meniscus.

Figure 29:
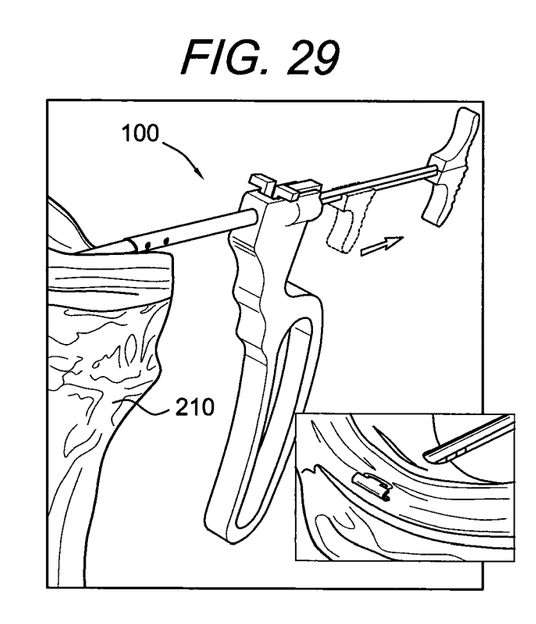

FIG. 29: The first trocar 10 is then removed from the cannula completely. A slight downward force on the first trocar 10 during removal ensures that it does not interfere with the second trocar 20.

Figure 30:
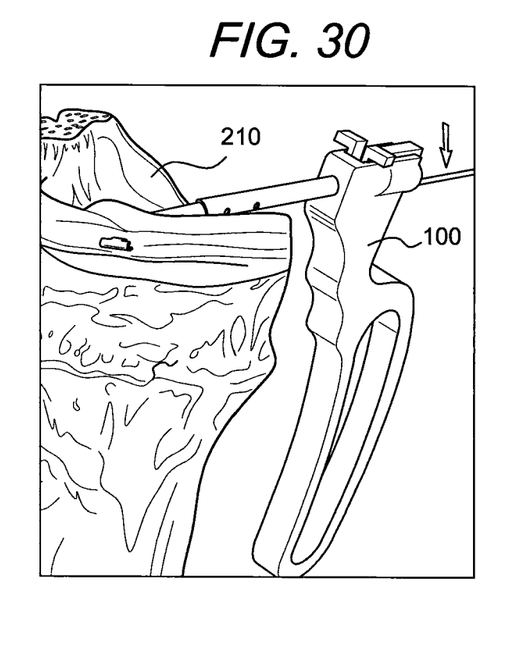

FIG. 30: Push down on the second trocar 20, to release it from the holding position. Next, the tip of the cannula is moved to the second insertion point so that the tip of the cannula is in contact with, but does not pierce, the meniscus.

Figure 31:
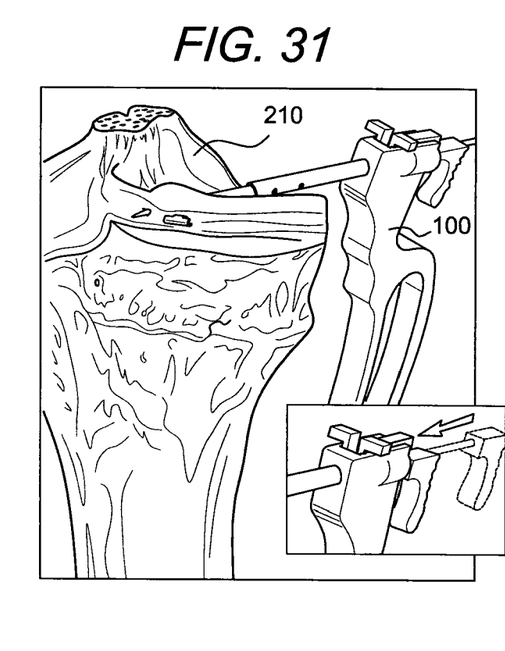
Figure 32:
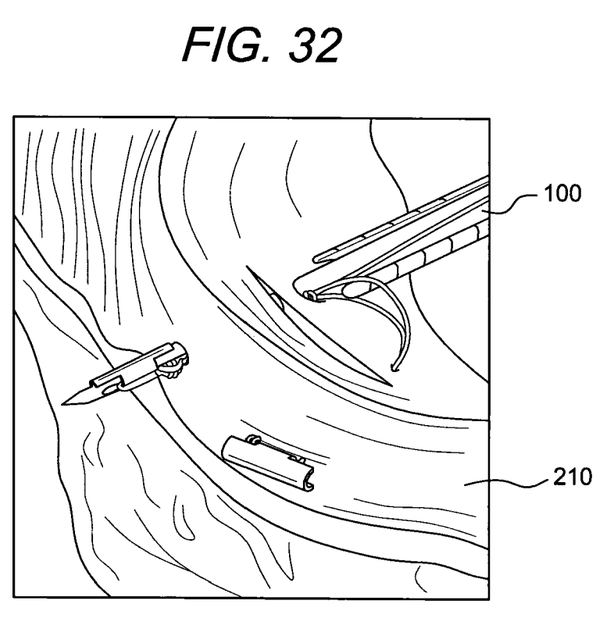

FIGS. 31 and 32: The second trocar 20 is advanced forward by pushing the trocar handle. The second trocar 20 is advanced through the meniscus until the trocar handle makes contact with the depth stop 30 and the cannula rests on the surface of the meniscus. Suture slack created by advancing the second trocar 20 may be reduced partially by gently tensioning external suture near the handle. Stop tensioning if resistance is felt.

Figure 33:
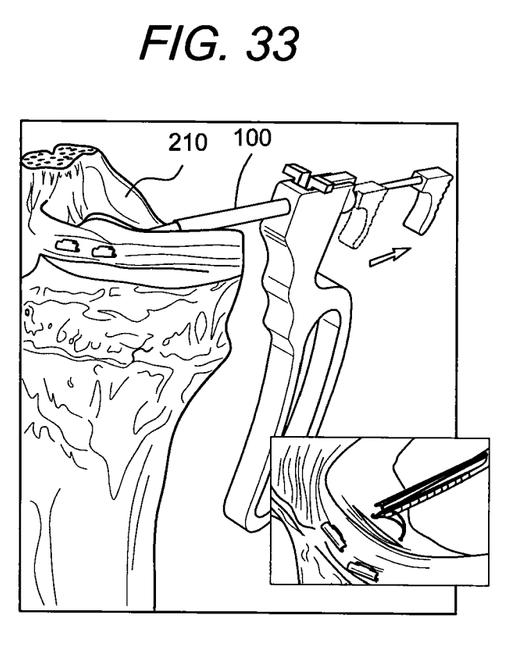

FIG. 33: The second trocar 20 is then fully removed from the cannula. While the second trocar 20 is being removed, the second implant 50 is released from the exterior surface of the second trocar 20. The second implant 50 then flips 90-degrees and becomes secured on the exterior surface of the meniscus adjacent to the first implant 40. The meniscal cinch assembly 100 is then removed from the joint. The external suture is tensioned to advance the knot to the meniscus.

Figure 34:
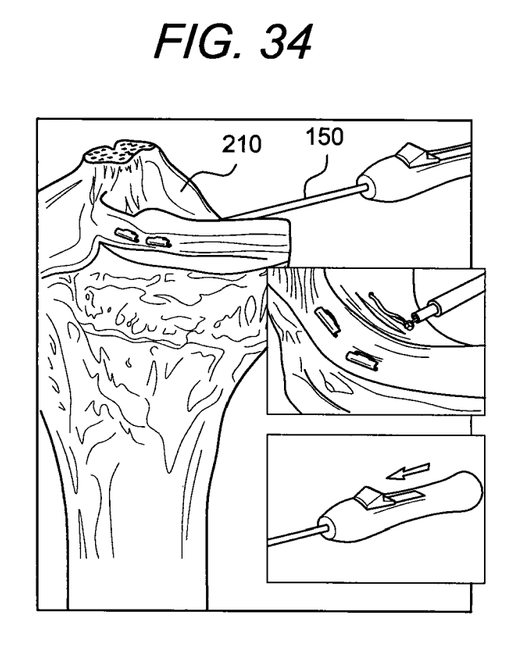

FIG. 34: The external suture is threaded through the tip of a suture passing instrument 150 such as a knot pusher-suture cutter instrument 150. The knot is pushed while pulling tension on the free end of suture. The knot is advanced until it is countersunk into the meniscal tissue.

Figure 35:
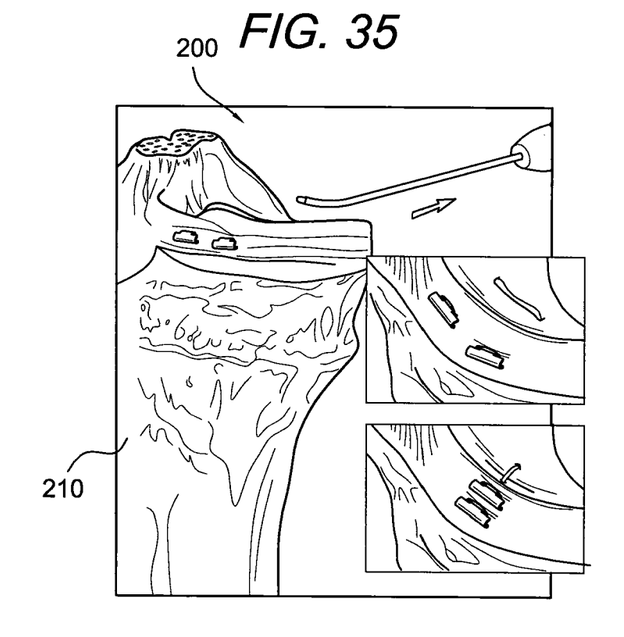

FIG. 35: The trigger on the handle of the knot pusher-suture cutter 150 is then advanced to cut the suture (the suture is pulled in line with the cutter 150 and rotation of handle is avoided while suture is cut). The cutter is removed to obtain the final construct 200 (with the implants in a horizontal orientation). Alternatively, the implants may be inserted in a vertical orientation (a vertical mattress stitch).

The meniscal cinch assembly 100 of the present invention allows surgeons to repair meniscus tears with an all-inside arthroscopic technique eliminating the need for accessory incisions required for traditional inside/out techniques that often result in additional morbidity. Based on the tear pattern and location, the meniscal cinch assembly 100 of the present invention gives surgeons the option of horizontal or vertical mattress repair with a flexible strand (such as a #2 FiberWire suture, for example). The present sliding knot and the FiberWire properties create a secure, low profile knot that can be countersunk into the meniscus. Depending on the exact location and pattern, posterior horn tears can be repaired through standard ipsilateral or contralateral arthroscopy portals. The meniscal cinch assembly 100 may be placed through the contralateral or accessory contralateral portal for tears involving the body of the meniscus.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A system for repairing tears in soft tissue, comprising:
   a first implant;
   a second implant;
   a flexible strand connecting the first implant and the second implant;
   a sliding knot in the flexible strand that is adjustable for reducing a length of the flexible strand that is located between the first implant and the second implant; and
   a delivery system for implanting the first implant and the second implant into the soft tissue, wherein the delivery system includes:
   a handle;
   an elongated shaft connected to the handle;
   a trocar assembly movable within the elongated shaft, wherein the first implant and the second implant are carried through the elongated shaft by the trocar assembly; and
   a depth stop adjustable between a first position that corresponds to a first insertion distance the trocar assembly extends beyond a tip of the elongated shaft and a second position that corresponds to a second, different insertion distance the trocar assembly extends beyond the tip,
   wherein the trocar assembly includes a first trocar that is slidable within a lower slot of a first hole formed in the handle and a second trocar that is removably received within an upper slot of the first hole of the handle,
   wherein a first trocar handle of the first trocar abuts the depth stop when the depth stop is in the second position to limit movement of the first trocar beyond the second insertion distance.

2. The system of claim 1, wherein the first implant is carried by the first trocar and the second implant is carried by the second trocar.

3. The system of claim 1, wherein a second trocar handle of the second trocar abuts the depth stop when the depth stop is in the second position to limit movement of the second trocar beyond the second insertion distance.

4. The system of claim 1, wherein the upper slot of the first hole is connected to the lower slot of the first hole.

5. The system of claim 1, wherein the first trocar includes a first pointed tip that extends through a first cannulation of the first implant and the second trocar includes a second pointed tip that extends through a second cannulation of the second implant.

6. The system of claim 1, wherein the first trocar is removable from the lower slot, and after removing the first trocar, the second trocar is movable from the upper slot into the lower slot.

7. A system for repairing tears in soft tissue, comprising:
a first implant;
a second implant;
a flexible strand connecting the first implant and the second implant;
a sliding knot in the flexible strand that is adjustable for reducing a length of the flexible strand that is located between the first implant and the second implant; and
a delivery system for implanting the first implant and the second implant into the soft tissue, wherein the delivery system includes:
a handle;
an elongated shaft connected to the handle;
a trocar assembly movable within the elongated shaft, wherein the first implant and the second implant are carried through the elongated shaft by the trocar assembly; and
a depth stop adjustable between a first position that corresponds to a first insertion distance the trocar assembly extends beyond a tip of the elongated shaft and a second position that corresponds to a second, different insertion distance the trocar assembly extends beyond the tip,
wherein the trocar assembly includes a first trocar that is slidable within a lower slot of a first hole formed in the handle and a second trocar that is removably received within an upper slot of the first hole of the handle,
wherein the depth stop is slidable within a ratcheted groove formed in the handle of the delivery system.

8. The system of claim 7, wherein, in the first position, the depth stop engages a first set of teeth of the ratcheted groove, and in the second position, the depth stop engages a second set of teeth of the ratcheted groove.

9. The system of claim 8, wherein the depth stop includes a pair of squeezable tabs that are movable toward one another to adjust the depth stop between the first position and the second position, and the pair of squeezable tabs are configured to engage the first set of teeth in the first position and to engage the second set of teeth in the second position.

10. A system for repairing tears in soft tissue, comprising:
a first implant;
a second implant;
a flexible strand connecting the first implant and the second implant;
a sliding knot in the flexible strand that is adjustable for reducing a length of the flexible strand that is located between the first implant and the second implant; and
a delivery system for implanting the first implant and the second implant into the soft tissue, wherein the delivery system includes:
a handle;
an elongated shaft connected to the handle;
a trocar assembly movable within the elongated shaft, wherein the first implant and the second implant are carried through the elongated shaft by the trocar assembly; and
a depth stop adjustable between a first position that corresponds to a first insertion distance the trocar assembly extends beyond a tip of the elongated shaft and a second position that corresponds to a second, different insertion distance the trocar assembly extends beyond the tip,
wherein the trocar assembly includes a first trocar that is slidable within a lower slot of a first hole formed in the handle and a second trocar that is removably received within an upper slot of the first hole of the handle,
wherein the depth stop includes an alignment pin received within an alignment pin hole formed in the handle.

11. The system of claim 10, wherein the alignment pin hole is a separate hole from the first hole.

12. A system for repairing tears in soft tissue, comprising:
a first implant;
a second implant;
a flexible strand connecting the first implant and the second implant;
a sliding knot in the flexible strand that is adjustable for reducing a length of the flexible strand that is located between the first implant and the second implant; and
a delivery system for implanting the first implant and the second implant into the soft tissue, wherein the delivery system includes:
a handle;
an elongated shaft connected to the handle;
a trocar assembly movable within the elongated shaft, wherein the first implant and the second implant are carried through the elongated shaft by the trocar assembly; and
a depth stop adjustable between a first position that corresponds to a first insertion distance the trocar assembly extends beyond a tip of the elongated shaft and a second position that corresponds to a second, different insertion distance the trocar assembly extends beyond the tip,
wherein the trocar assembly includes a first trocar that is slidable within a lower slot of a first hole formed in the handle and a second trocar that is removably received within an upper slot of the first hole of the handle,
wherein the first trocar is received through a lower slot of a second hole formed in the depth stop and the second trocar is received through an upper slot of the second hole.

13. A system for repairing tears in soft tissue, comprising:
a first implant;
a second implant;
a flexible strand connecting the first implant and the second implant;

a sliding knot in the flexible strand that is adjustable for reducing a length of the flexible strand that is located between the first implant and the second implant; and a delivery system for implanting the first implant and the second implant into the soft tissue, wherein the delivery system includes:

a handle;

an elongated shaft connected to the handle;

a trocar assembly movable within the elongated shaft, wherein the first implant and the second implant are carried through the elongated shaft by the trocar assembly; and a depth stop adjustable between a first position that corresponds to a first insertion distance the trocar assembly extends beyond a tip of the elongated shaft and a second position that corresponds to a second, different insertion distance the trocar assembly extends beyond the tip, wherein the trocar assembly includes a first trocar that is slidable within a lower slot of a first hole formed in the handle and a second trocar that is removably received within an upper slot of the first hole of the handle, wherein the depth stop includes a first depth stop portion received within a groove formed in the handle and a second depth stop portion that extends rearward of the first depth stop portion and in direction opposite of the elongated shaft.

14. The system of claim 13, wherein the first trocar and the second trocar extend through the second depth stop portion.

15. The system of claim 13, wherein a first trocar handle of the first trocar abuts the second depth stop portion when the depth stop is in the second position to limit movement of the first trocar beyond the second insertion distance.

16. The system of claim 13, wherein the depth stop includes an alignment pin received within an alignment pin hole formed in the second depth stop portion.

17. A system for repairing tears in soft tissue, comprising:

a first implant;

a second implant;

a flexible strand connecting the first implant and the second implant;

a sliding knot in the flexible strand that is adjustable for reducing a length of the flexible strand that is located between the first implant and the second implant; and a delivery system for implanting the first implant and the second implant into the soft tissue, wherein the delivery system includes:

a handle;

an elongated shaft connected to the handle;

a trocar assembly movable within the elongated shaft, wherein the first implant and the second implant are carried through the elongated shaft by the trocar assembly; and a depth stop adjustable between a first position that corresponds to a first insertion distance the trocar assembly extends beyond a tip of the elongated shaft and a second position that corresponds to a second, different insertion distance the trocar assembly extends beyond the tip, wherein the trocar assembly includes a first trocar that is slidable within a lower slot of a first hole formed in the handle and a second trocar that is removably received within an upper slot of the first hole of the handle, wherein the upper slot is located axially between the lower slot and a ratcheted groove formed in the handle.

18. A system for repairing tears in soft tissue, comprising:

a first implant;

a second implant;

a flexible strand connecting the first implant and the second implant;

a sliding knot in the flexible strand that is adjustable for reducing a length of the flexible strand that is located between the first implant and the second implant; and a delivery system for implanting the first implant and the second implant into the soft tissue, wherein the delivery system includes:

a handle;

an elongated shaft connected to the handle;

a trocar assembly movable within the elongated shaft, wherein the first implant and the second implant are carried through the elongated shaft by the trocar assembly; and a depth stop adjustable between a first position that corresponds to a first insertion distance the trocar assembly extends beyond a tip of the elongated shaft and a second position that corresponds to a second, different insertion distance the trocar assembly extends beyond the tip, wherein the trocar assembly includes a first trocar that is slidable within a lower slot of a first hole formed in the handle and a second trocar that is removably received within an upper slot of the first hole of the handle, wherein the second trocar is snapped into the upper slot, and after removing the first trocar, is downwardly slidable to position the second trocar within the lower slot.

* * * * *